United States Patent [19]

Bergot et al.

[11] Patent Number: 5,366,860

[45] Date of Patent: Nov. 22, 1994

[54] SPECTRALLY RESOLVABLE RHODAMINE DYES FOR NUCLEIC ACID SEQUENCE DETERMINATION

[75] Inventors: B. John Bergot, Redwood City; Vergine Chakerian, San Mateo; Charles R. Connell, Redwood City, all of Calif.; J. Scott Eadie, Indianapolis, Ind.; Steven Fung, Palo Alto, Calif.; N. Davis Hershey, San Carlos, Calif.; Linda G. Lee, Palo Alto, Calif.; Steven M. Menchen, Fremont, Calif.; Sam L. Woo, Redwood City, Calif.

[73] Assignee: Applied Biosystems, Inc., Foster City, Calif.

[21] Appl. No.: 415,050

[22] Filed: Sep. 29, 1989

[51] Int. Cl.$^5$ .................................. C12Q 1/68
[52] U.S. Cl. ....................... 435/6; 536/25.32
[58] Field of Search ............................. 435/6

[56] References Cited

U.S. PATENT DOCUMENTS 4,962,037  10/1990  Jett et al. ................... 435/6

OTHER PUBLICATIONS

Chem. Abstr. vol. 109, No. 18, Menchen et al. 1988 Abstr. No. 151451t.
Chem. Abstr. vol. 108, No. 23, Sproat, 1987, Abstr. No. 199501r.
Biol. Abstr. vol. 63, Kuehner, 1976 Abstr. No. 63352.
Biol. Abstr., vol. 83 Ansorge, et al., 1987, Abstr. No. 104132.
Kubin et al., *J. Luminescence*, 27 (1982), pp. 455–462.
Karstens et al., *J. Phys. Chem.*, 1980, vol. 84, No. 14, pp. 1871–1872.
Connell et al., Biotechniques, vol. 5, pp. 342–348 (1987).
Karger et al., Nucleic Acids Research, vol. 19, pp. 4955–4962 (1991).
Wehry, Chapters 3 and 4, in Guilbault, editor, Practical Fluorescence, 2nd Ed. (Marcel Dekker, New York, 1990).
Haugland chapter 2, in Steiner, editor, Excited States of Biopolymers (Plenum Press, New York, 1983).
Haugland, Handbook of Fluorescent Probes and Research Chemicals, (Molecular Probes, Inc., Eugene, 1989) excerpts showing emission max.
Kodak Laboratory Chemicals Catalog 1981–1982 (Eastman Kodak Co., Rochester, 1981) excerpts showing emission max of fl. dyes.

*Primary Examiner*—Christopher S. F. Low
*Assistant Examiner*—Keith D. Hendricks
*Attorney, Agent, or Firm*—Stephen C. Macevicz; Peter Dehlinger; Vince Powers

[57] ABSTRACT

A spectrally resolvable set of rhodamine dyes are provided for use in the chain termination method of nucleic acid sequencing. A different rhodamine dye from the group consisting of tetramethylrhodamine, rhodamine X, rhodamine 6G, and rhodamine 110 is attached to the base of each of the dideoxynucleotides used in the sequencing method by way of an alkynylamino linker. Preferably, the labeled dideoxynucleotides are incorporated into the growing DNA chains by Taq DNA polymerase.

10 Claims, No Drawings

5,366,860

SPECTRALLY RESOLVABLE RHODAMINE DYES FOR NUCLEIC ACID SEQUENCE DETERMINATION

FIELD OF THE INVENTION

The invention relates generally to methods for determining the sequence of a nucleic acid, and more particularly, to use of rhodamine dyes to identify similarly sized DNA fragments separated by gel electrophoresis.

BACKGROUND

The ability to determine DNA sequences is crucial for understanding the function and control of genes and for applying many of the basic techniques of molecular biology. Native DNA consists of two linear polymers, or strands of nucleotides. Each strand is a chain of nucleosides linked by phosphodiester bonds. The two strands are held together in an antiparallel orientation by hydrogen bonds between complementary bases of the nucleotides of the two strands: deoxyadenosine (A) pairs with thymidine (T) and deoxyguanosine (G) pairs with deoxycytidine (C).

Presently there are two basis approaches to DNA sequence determination: the dideoxy chain termination method, e.g. Sanger et al, *Proc. Natl. Acad. Sci.*, Vol. 74, pgs. 5463–5467 (1977); and the chemical degradation method, e.g. Maxam et al, *Proc. Natl. Acad. Sci.*, Vol. 74, pgs. 560–564 (1977). The chain termination method has been improved in several ways, and serves as the basis for all currently available automated DNA sequencing machines, e.g. Sanger et al, *J. Mol. Biol.*, Vol. 143, pgs. 161–178 (1980); Schreier et al, *J. Mol. Biol.*, Vol. 129, pgs. 169–172 (1979); Smith et al, *Nucleic Acids Research*, Vol. 13, pgs. 2399–2412 (1985); Smith et al, *Nature*, Vol. 321, pgs. 674–679 (1987); Prober et al, *Science*, Vol. 238, pgs. 336–341 (1987), Section II, *Meth. Enzymol.*, Vol. 155, pgs. 51–334 (1987); Church et al, *Science*, Vol. 240 pgs. 185–188 (1988); and Connell et al, *Biotechniques*, Vol. 5, pgs. 342–348 (1987).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis. In most automated DNA sequencing machines, fragments having different terminating bases are labeled with different fluorescent dyes, which are attached either to a primer, e.g. Smith et al (1987, cited above), or to the base of a terminal dideoxynucleotide, e.g. Prober et al (cited above). The labeled fragments are combined and loaded onto the same gel column for electrophoretic separation. Base sequence is determined by analyzing the fluorescent signals emitted by the fragments as they pass a stationary detector during the separation process.

Obtaining a set of dyes to label the different fragments is a major difficulty in such DNA sequencing systems. First, it is difficult to find three or more dyes that do not have significantly overlapping emission bands, since the typical emission band halfwidth for organic fluorescent dyes is about 40–80 nanometers (nm) and the width of the visible spectrum is only about 350–400 nm. Second, even when dyes with non-overlapping emission bands are found, the set may still be unsuitable for DNA sequencing if the respective fluorescent efficiencies are too low. For example, Pringle et al, DNA Core Facilities Newsletter, Vol. 1, pgs. 15–21 (1988), present data indicating that increased gel loading cannot compensate low fluorescent efficiencies. Third, when several fluorescent dyes are used concurrently, excitation becomes difficult because the absorption bands of the dyes are often widely separated. The most efficient excitation occurs when each dye is illuminated at the wavelength corresponding to its absorption band maximum. When several dyes are used one is often forced to make a trade off between the sensitivity of the detection system and the increased cost of providing separate excitation sources for each dye. Fourth, when the number of differently sized fragments in a single column of a gel is greater than a few hundred, the physiochemical properties of the dyes and the means by which they are linked to the fragments become critically important. The charge, molecular weight, and conformation of the dyes and linkers must not adversely effect the electrophoretic mobilities of closely sized fragments so that extensive band broadening occurs or so that band positions on the gel become reversed, thereby destroying the correspondence between the order of bands and the order of the bases in the nucleic acid whose sequence is to be determined. Finally, the fluorescent dyes must be compatible with the chemistry used to create or manipulate the fragments. For example, in the chain termination method, the dyes used to label primers and/or the dideoxy chain terminators must not interfer with the activity of the polymerase or reverse transcriptase employed.

Because of these severe constraints only a few sets of fluorescent dyes have been found that can be used in automated DNA sequencing and in other diagnostic and analytical techniques, e.g. Smith et al (1985, cited above); Prober et al (cited above); Hood et al, European patent application 8500960; and Connell et al (cited above).

In view of the above, many analytical and diagnostic techniques, such as DNA sequencing, would be significantly advanced by the availability of new sets of fluorescent dyes (1) which are physiochemically similar, (2) which permit detection of spacially overlapping target substances, such as closely spaced bands of DNA on a gel, (3) which extend the number of bases that can be determined on a single gel column by current methods of automated DNA sequencing, (4) which are amenable for use with a wide range of preparative and manipulative techniques, and (5) which otherwise satisfy the numerous requirements listed above.

SUMMARY OF THE INVENTION

The invention is directed to a method of DNA sequencing wherein electrophoretically separated DNA fragments having different 3'-terminal nucleotides are identified by different rhodamine dyes. In particular, the invention includes the rhodamine-labeled nucleotides defined below and their use in the method of the invention. The invention is based in part on the discovery of a set of spectrally resolvable rhodamine dyes linked to chain-terminating nucleotides that are readily incorporated into growing DNA chains by DNA polymerases, particularly Taq DNA polymerase. As used herein the term "chain terminating nucleotide" refers to a nucleotide or analog thereof which prevents further polynucleotide chain elongation, or extension, after it has been incorporated into a growing DNA chain by a DNA polymerase. Usually, the chain terminating property of such nucleotides is due to the absence or modification of the 3' hydroxyl of the sugar moiety. Preferably, the chain-terminating nucleotides are 2',3'-dideoxynucleotides.

As used herein the term "spectrally resolvable" in reference to a set of dyes means that the fluorescent emission bands of the dyes are sufficiently distinct, i.e. sufficiently non-overlapping, that target substances to which the respective dyes are attached, e.g. polynucleotides, can be distinguished on the basis of the fluorescent signal generated by the respective dyes by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in *Flow Cytometry: Instrumentation and Data Analysis* (Academic Press, New York, 1985).

Whenever the rhodamines of the invention are used to label 3'-terminal nucleotides, an important feature of the invention is the virtually equivalent contributions to electrophoretic mobility of the DNA fragments made by the four dyes. This result is unexpected because it is believed that conformational interactions between the label and the adjacent nucleotides are primarily responsible for the variability in electrophoretic mobility of labeled DNA fragments. It was expected that dye-labeled primers would always cause less variability in electrophoretic mobilities since the dye would always interact with the same sequence of nucleotides. However, part of the present invention is the discovery that fragments with 3'-labeled nucleotides have much less variability in electrophoretic mobilities than equivalent fragments with dye-labeled primers.

DETAILED DESCRIPTION OF THE INVENTION

The spectrally resolvable set of rhodamine dyes of the invention consists of tetramethylrhodamine, rhodamine X, rhodamine 110, and rhodamine 6G, which are defined by Formulas I–IV, respectively. Throughout, the *Colour Index* (Association of Textile Chemists, 2nd Ed., 1971) carbon numbering scheme is used, i.e. primed numbers refer to carbons in the xanthene structure and unprimed numbers refer to carbons in the 9'-phenyl.

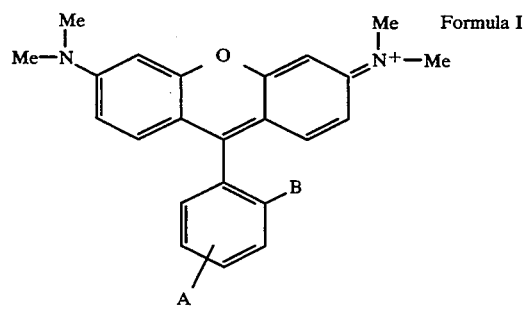

Formula I

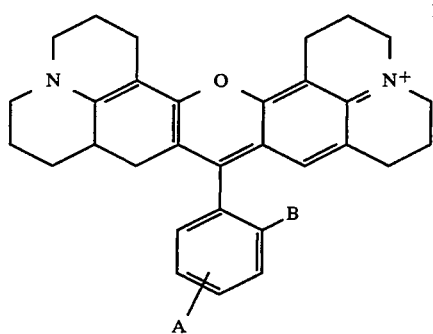

Formula II

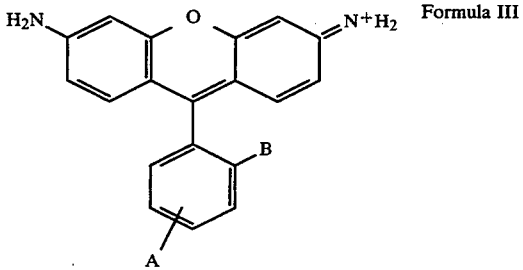

Formula III

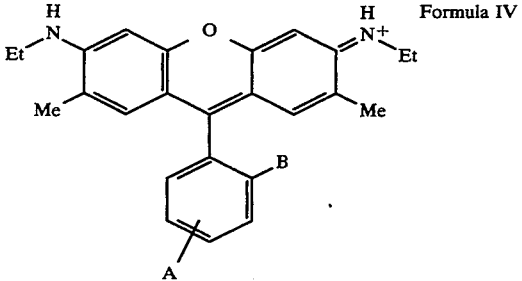

Formula IV wherein:

A is a group, such as carboxyl, sulfonyl, or amino, that may be converted into a linking functionality; and B is an anionic acidic group, preferably carboxyl or sulfonyl, and most preferably carboxyl.

Preferably, the rhodamine-labeled chain-terminating nucleotides of the invention have the following form:

XTP—L—R wherein XTP is a chain-terminating nucleoside triphosphate; R is a rhodamine dye selected from the group consisting of tetramethylrhodamine, rhodamine X, rhodamine 110, and rhodamine 6G; and L is a linking group between the base of the nucleoside triphosphate and the rhodamine dye.

XTP is an analog of the natural nucleoside triphosphate substrate of the DNA polymerase employed which prevents further chain elongation after incorporation. Several such analogs are available for each of the four natural nucleoside triphosphates, e.g. Hobbs et al (cited above) gives a list. Preferably, XTP is a 2',3'-dideoxynucleoside triphosphate. More preferably, XTP is selected from the group consisting of 2',3'-dideoxy-7-deazaadenosine triphosphate, 2',3'-dideoxycytidine triphosphate, 2',3'-dideoxy-7-deazaguanosine, 2',3'-dideoxyuridine triphosphate, and 2',3'-dideoxy-7-deazainosine triphosphate. As used herein, the term "dideoxynucleoside" includes nucleoside analogs whose sugar moieties are either cyclic or acyclic. Conventional numbering is used whenever specific carbon atoms of a base or sugar of a nucleoside are referred to, e.g. Kornberg, *DNA Replication* (Freeman, San Francisco, 1980).

L can take on a number of different forms such that the length and rigidity of the linkage between the dideoxynucleotide and the dye can vary greatly. For example, several suitable base labeling procedures have been reported that can be used with the invention, e.g. Gibson et al, *Nucleic Acids Research*, Vol. 15, pgs. 6544–6467 (1987); Gebeyehu et al, *Nucleic Acids Research*, Vol. 15, pgs. 4513–4535 (1987); Haralambidis et al, *Nucleic Acids Research*, Vol. 15, pgs. 4856–4876 (1987); and the like. Preferably, L is formed by reacting an N-hydroxysuccinimide (NHS) ester of a dye of the invention with an alkynylamino-derivatized base of a dideoxynucleotide. In this case, L is taken as the moiety between (1) the 5- or 6-carbon of the rhodamine and (2) the carbon of the base to which the rhodamine is attached. Preferably, L is 3-carboxyamino-1-propynyl. The synthesis of such alkynylamino-derivatized dideoxynucleotides of cytosine, thymine, and adenine is taught by Hobbs et al in European patent application No. 87305844.0 and Hobbs, *J. Org. Chem.*, Vol. 54, pg. 3420 (1989), which are incorporated herein by reference. Briefly, the alkynylamino-derivatized dideoxynucleotides are formed by placing the appropriate halodideoxynucleoside (usually 5-iodopyrimidine and 7-iodo-7-deazapurine dideoxynucleosides as taught by Hobbs et al (cited above)) and Cu(I) in a flask, flushing with Ar to remove air, adding dry DMF, followed by addition of an alkylamine, triethylamine and Pd(0). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Synthesis of the alkynylamine-derivatized dideoxyguanosine according to the above reference requires specially modified quanine precursor (6-methoxy-2-methylthio-7-deazapurine, X), which is obtained from the starting material, 6-hydroxy-2-methylthio-7-diazapurine, XX. Conversion of XX to 6-chloro-2-methylthio-7-deazapurine, XXX, according to Robins and Noell (*J. Heterocyclic Chem.*, Vol. 1, pg. 34 (1964)), followed by displacement of the chloro substituent with methoxide (sodium salt in refluxing methanol) yields X:

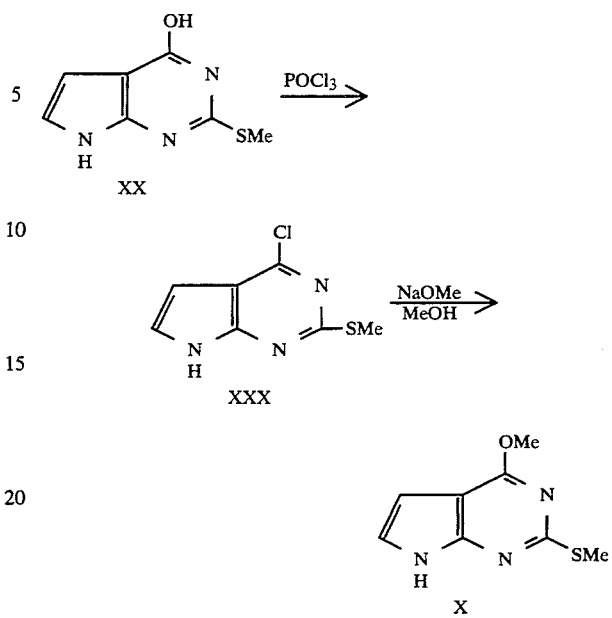

Preferably, the rhodamine NHS esters are synthesized in accordance with the teachings of U.S. patent application No. 06/941,985. Important features of the method of synthesizing the rhodamine NHS esters include (1) the reaction condition of having substantially stoichiometric amounts of di-N-succinimidylcarbonate (DSC) and 4-dimethylaminopyridine (DMAP) present for esterification of the 5- or 6- forms of the rhodamine dyes to produce high yields of product at room temperature, and (2) the treatment of the freshly synthesized product with an acidic compound, preferably having a $pK_a$ or less than 5, to prevent conversion back into reactants. The general reaction scheme of the invention is defined by Formula IX:

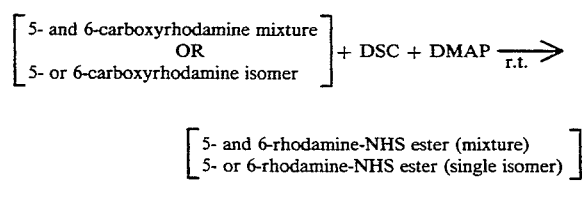

FORMULA IX

The methods comprise reacting the acid form of a 5- or 6-carboxylrhodamine (either as a mixture of isomers, or as pure isomers) with equivalent amounts of DSC and DMAP in a polar aprotic solvent to form the carboxyl N-hydroxysuccinimide ester. Suitable polar aprotic solvents include N,N-dimethylformamide (DMF), pyridine, hexamethylphosphoramide (HMPA), or the like. Most preferably, DMF is used as the reaction solvent. The isomerically mixed NHS esters can be separated into their individual isomers for further use. Most preferably, in order to conserve reagents, the acid forms of the 5- or 6-carboxylrhodamines are first separated into their individual isomers by standard separative techniques, e.g. Edmundson et al., *Molecular Immunology*, Vol. 21, pg. 561 (1984), and then the individual 5- or 6- carboxyl isomers are reacted as described above to form the 5- or 6-carboxyl NHS esters, respectively, which are separated from the reaction mixture, again using standard techniques.

Preferably, the freshly synthesized rhodamine NHS ester is treated with a volatile, organic-soluble acid with pK<5; and more preferably, a volatile, organic-soluble acidic compound with pK<1, such as HCl or HBr in methanol, or most preferably, trifluoroacetic acid.

Some isomeric mixtures of rhodamine dyes for use with the invention are available commercially, e.g. Molecular Probes, Inc. (Eugene, Ore.), and others can be synthesized in accordance with the teachings of U.S. Pat. Nos. 2,242,572; 2,153,059; 3,822,270; 3,932,415; and 4,005,092, all of which are incorporated by reference.

The rhodamines of the invention are particularly well suited for identifying classes of polynucleotides that have been subjected to a biochemical separation procedure, such as gel electrophoresis, where a series of closely spaced bands or spots of polynucleotides having similar physiochemical properties, e.g. size, conformation, charge, hydrophobicity, or the like, are present in a linear or planar arrangement. As used herein, the term "bands" includes any spacial grouping or aggregation of polynucleotide on the basis of similar or identical physiochemical properties. Usually bands arise in the separation of dye-polynucleotide conjugates by gel electrophoresis.

Preferably, classes of polynucleotides identified in accordance with the invention are defined in terms of terminal nucleotides so that a correspondence is established between the four possible terminal bases and the four spectrally resolvable dyes. In particular, classes of polynucleotides arise in the context of the chain termination methods of DNA sequencing, where dye-polynucleotide conjugates are separated according to size by gel electrophoresis, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 (Springer-Verlag, Berlin, 1984). Preferably the type of gel is polyacrylamide having a concentration (weight to volume) of between about 2-20 percent. More preferably, the polyacrylamide gel concentration is between about 4-8 percent. Preferably the gel includes a strand separating, or denaturing, agent. Detailed procedures for constructing such gels are given by Maniatis et al., "Fractionation of Low Molecular Weight DNA and RNA in Polyacrylamide Gels Containing 98% Formamide or 7M Urea, " in *Methods in Enzymology*, Vol. 65, pgs. 299-305 (1980); Maniatis et al., "Chain Length Determination of Small Double- and Single-Stranded DNA Molecules by Polyacrylamide Gel Electrophoresis," *Biochemistry*, Vol. 14, pgs. 3787-3794, (1975); and Maniatis et al., *Molecular Cloning: A Laboratory Manual* (Cold Spring Harbor Laboratory, New York 1982), pgs. 179-185. Accordingly these references are incorporated by reference. The optimal gel concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. Preferably, during polynucleotide chain extension deoxyinosine triphosphate is substituted for deoxyguanosine triphosphate to avoid so called "band compression" during electrophoresis, e.g. Mills et al, *Proc. Natl. Acad. Sci.*, Vol. 76, pgs. 2232-2235 (1979). By way of example, polynucleotides having sizes in the range of between about 10-500 bases are separated and detected in accordance with the invention in the following gel: 6 percent polyacrylamide made from 19 parts to 1 part acrylamide to bis-acrylamide, formed in a Tris-borate EDTA buffer at pH 8.1 (measured at 25° C.) with 48 percent (weight/volume) urea. The gel is run at about 40° C.

The dye-polynucleotide conjugates on the gel are illuminated by standard means, e.g. high intensity mercury vapor lamps, lasers, or the like. Preferably, the dye-polynucleotides on the gel are illuminated by laser light generated by a argon ion laser, particularly the 488 and 514 nm emission lines of an argon ion laser. Several argon ion lasers are available commercially which lase simultaneously at these lines, e.g. Cyonics, Ltd. (Sunnyvale, Calif.) Model 2001, or the like.

An important feature of the invention is the DNA polymerase used for chain extension in the DNA sequencing procedure. Preferably, the polymerase used in the method of the invention is selected from the group consisting of Taq DNA polymerase, described by Innis et al, *Proc. Natl. Acad. Sci.*, Vol. 85, pgs. 9436-9440 (1988), with either a manganese or magnesium buffer; and T7 DNA polymerase with a manganese buffer, described by Tabor et al, *Proc. Natl. Acad. Sci.*, Vol. 86, pgs. 4076-4080 (1989). Generally, the single stranded DNA template containing the unknown sequence is prepared by standard techniques, e.g. in M13mp18 as described in the manual for the Applied Biosystems Model 370A DNA sequencing system. Likewise, the annealing reaction, wherein the primer is attached to the template, is carried out by standard protocols. The extension reaction, wherein different-sized DNA fragments are generated is optimized for the rhodamine-labeled dideoxynucleotides of the invention and the particular DNA polymerase used.

EXAMPLES

The following examples serve to illustrate the present invention. The concentrations of reagents, temperatures, and the values of other variable parameters are only to exemplify the invention and are not to be considered limitations thereof.

EXAMPLE 1

6-TMR-NHS

6-TMR acid was separated from a mixture of the 5- and 6-TMR acid isomers by column chromatography. 8.82 mg of 6-TMR acid and 10.5 mg of DSC were dissolved in 0.5 ml of dry DMF under argon. 0.09 ml of a 0.5 molar solution of DMAP in tetrahydrofuran (THF) was added in one portion. After 2 hours at room temperature, the mixture was taken into 50 ml of chloroform and washed three times with a 1:1 solution of brine:water. The chloroform was evaporated and the residue was purified on a 20 g silica gel column (300:30:8 methylene chloride:methanol:acetic acid elution). Fractions with $R_f$ of about 0.4 were evaporated to dryness, yielding 8.6 mg of 6-TMR-NHS as its acetic acid salt.

EXAMPLE 2

5-TMR-NHS

5-TMR-NHS was prepared from 82.3 mg of 5-TMR acid, 75 mg of DSC, 0.70 ml of 0.5 molar DMAP in THF in 2 ml dry DMF, as described in Example 1.

EXAMPLE 3

6-ROX-NHS

6-ROX acid was separated from a mixture of 5- and 6-acid isomers by column chromatography. 46.2 mg of 6-ROX acid and 58 mg of DSC were dissolved in 2 ml of dry DMF under argon and 0.45 ml of a 0.5 molar solution of DMAP in THF was added in one portion. After 1.5 hours at room temperature, the mixture was taken into 100 ml chloroform and washed four times with a 1:1 solution of brine:water. The chloroform was evaporated and the residue was purified on a 40 g silica gel column (300:30:8 methylene chloride:methanol:acetic acid elution). Fractions with $R_f$ of about 0.5 were evaporated to dryness, yielding 56.4 mg of 6-ROX-NHS as its acetic acid salt.

EXAMPLE 4

5-ROX-NHS

5-ROX-NHS was prepared from 27.4 mg of 5-ROX acid, 30.2 mg of DSC, 0.24 ml of 0.5 molar DMAP in THF in 1.0 ml dry DMF, as described in Example 3.

EXAMPLE 5

A Stable Formulation of Rhodamine NHS esters a) 0.44 mg of 6-carboxy-X-rhodamine NHS ester from Example 3 and 80 ul of 0.01 molar ethanol amine in methanol were combined. Reverse phase HPLC of the reaction mixture with acetonitrile and 0.1 molar triethylammonium acetate buffer (pH=7.0) showed that the product was composed of 70% X-rhodamine acid and 30% of X-rhodamine NHS ester (observed as the ethanolamide of 6-carboxy-X-rhodamine from its reaction with ethanol amine).

b) 0.15 g of 6-carboxy-X-rhodamine NHS ester from Example 3 were dissolved in 100 m. of chloroform; the chloroform solution was washed two times with 0.5 molar sodium bicarbonate, dried with sodium sulfate, filtered, treated with 0.1 ml of acetic acid and evaporated to dryness. 0.35 mg of the product was treated exactly as in a); reverse phase HPLC showed 20% 6-carboxy-X-rhodamine acid and 80% of 6-carboxy-X-rhodamine NHS ester.

c) 0.15 g of 6-carboxy-X-rhodamine NHS ester from Example 3 was treated exactly as in b), except that trifluoroacetic acid was substituted for acetic acid. 0.19 mg of the resulting solid were treated exactly as in a); reverse phase HPLC showed <5% 6-carboxy-X-rhodamine acid and >95% 6-carboxy-X-rhodamine NHS ester.

EXAMPLE 6

Preparation of R6G-labeled 7-deaza-2',3'-dideoxyadenosine triphosphate (ddA-5-R6G)

To 2.0 umoles of 7-(3''-amino-1''-propynyl)-7-deaza-2',3'-dideoxyadenosine triphosphate (lyophilized), obtained as described, is added 100 ul of DMF, 3 mg of 5-rhodamine 6G-NHS ester and 50 ul of 1.0M triethylammonium carbonate, pH 8.95. This was vortexed and allowed to stand at room temperature overnight. The mixture was then purified by HPLC on a AX-300 220×4.6 mm, 7 micron column with 1.5 ml per minute flow rate. Starting elution was at 60% 0.1M triethylammonium carbonate, pH 7.0, 40% $CH_3CN$ with a linear gradient to 60% 1.2M triethylammonium carbonate, pH 7.5, 40% $CH_3CN$ over 40 minutes. The solvent was removed from the collected product by evaporation under vacuum. The residue was dissolved in 0.01M triethylammonium acetate pH 7.0 and quantified.

EXAMPLE 7

Preparation of ROX-labeled 2',3'-dideoxycytidine triphosphate (ddC-6ROX)

To 3.6 umoles of 5-(3''-amino-1''-propynyl)-2',3'-dideoxycytidine triphosphate, (obtained as described) in 150 ul of $H_2O$ was added 5 mg of 6-rhodamine X-NHS ester in 60 ul of DMSO and 50 ul of 1.0M triethylammonium carbonate pH 8.95. This was vortexed and allowed to stand at room temperature overnight. The product was purified as in Example 6.

EXAMPLE 8

Preparation of R110-labeled 2',3'-dideoxyinosine triphosphate (ddG-5R110)

To 1.3 umoles of 7-(3''-amino-1''-propynyl)-7-deaza-2',3'-dideoxyguanosine triphosphate (lyophilized), obtained as described, was added 100 ul of DMF, 4 mg of 5-rhodamine 110-NHS ester, and 100 ul of 1.0M triethylammonium carbonate pH 8.95. This was vortexed and allowed to stand overnight at room temperature. The product was purified as in Example 6.

EXAMPLE 9

Preparation of TMR-labeled 2',3'-dideoxythymidine triphosphate (ddT-6TMR)

3.1 umoles of 5-(3''-amino-1''-propynyl)-2',3'-dideoxyuridine triphosphate in 150 ul of $H_2O$, obtained as described, was mixed with 150 ul of DMF, 100 ul of 1.0M triethylammonium carbonate pH 8.95, and 4 mg of 6-TMR-NHS ester. This was vortexed and allowed to stand overnight at room temperature. The produce was purified as in Example 6.

EXAMPLE 10

DNA sequence analysis using rhodamine-labeled dideoxynucleotides and Taq DNA polymerase with a magnesium buffer The rhodamine labeled dideoxynucleotides prepared in Examples 6–9 were used to label DNA fragments in chain termination sequencing using an Applied Biosystems (Foster City, Calif.) Model 370A automated DNA sequencer. The manufacturer's protocol (User Bulletin DNA Sequencer Model 370, Issue No. 2, Aug. 12, 1987), which is incorporated by reference, was followed for obtaining M13mp18 single stranded template. (The M13 itself served as a test sequence). The M13 universal primer was employed. The following solutions were prepared: 5X Taq Mg Buffer (50 mM Tris-Cl pH 8.5, 50 mM $MgCl_2$, 250 mM NaCl); Dye-Terminator Mix (2.7 uM ddG-5R110, 9.00 uM ddA-5R6G, 216.0 uM ddT-6TMR, and 54.0 uM ddC-6ROX); and DNTP Mix (500 uM dITP, 100 uM dATP, 100 uM dTTP, and 100 uM dCTP). The annealing reaction was carried out by combining in a microcentrifuge tube 3.6 ul of 5X Taq Mg Buffer, 0.4 pmol DNA template, 0.8 pmol primer, and water to a volume of 12.0 ul. The mixture was incubated at 55°–65° C. for 5–10 minutes, cooled slowly over a 20–30 minute period to a temperature between 4°–20° C., then centrifuged once to collect condensation, mixed, and placed on ice. To the mixture was then added 1.0 ul dNTP Mix, 2.0 ul Dye-Terminator Mix, 4 units of Taq polymerase, and water to bring the volume to 18.0 ul. The mixture was incubated for 30 minutes at 60° C., then placed on ice and combined with 25.0 ul of 10 mM EDTA pH 8.0 to quench the reaction. The DNA in the mixture was then purified in a spin column (e.g. a 1 ml Sephadex G-50 column, such as a Select-D from 5 Prime to 3 Prime, West Chester, Pa.) and ethanol precipitated (by adding 4 ul 3M sodium acetate pH 5.2 and 120 ul 95% ethanol, incubating on ice for 10 minutes, centrifuging for 15 minutes, decanting and draining the supernatant, resuspending in 70% ethanol, vortexing, centrifuging for 15 minutes, decanting and draining the supernatant, and drying in a vacuum centrifuge for 5 minutes). The precipitated DNA was then resuspended in 3 ul of a solution consisting of 5 parts deionized formamide and 1 part 50 mM EDTA pH 8.0 and vortexed thoroughly. Prior to loading on the gel the mixture was incubated at 90° C. for 2 minutes to denature the DNA. Over 450 bases of the M13 plasmid were correctly identified by the base calling routine of the Model 370A automated sequencer.

EXAMPLE 11

DNA sequence analysis using rhodamine-labeled dideoxynucleotides and T7 DNA polymerase with a manganese buffer The sequencing reaction is carried out as in Example 10, except that in place of 5X Taq Mg Buffer 5X T7 Mn Buffer (100 mM Tris-Cl pH 7.5, 75 mM sodium isocitrate, 10 mM $MnCl_2$, 250 mM NaCl) is used, the Dye-Terminator Mix consists of 1.8 uM ddG-5R110, 5.4 uM ddA-5R6G, 5.8 mM ddt-6TMR, and 9.0 uM ddC-6ROX, the dNTP Mix consists of 750 uM dITP, 150 uM dATP, 150 uM dTTP, and 150 uM dCTP, and the extension reaction is carried out at 37° C. for 10 minutes.

EXAMPLE 12

DNA sequence analysis using rhodamine-labeled dideoxynucleotides and Taq DNA polymerase with a manganese buffer The sequencing was carried out as in Example 10, except in place of 5X Taq Mg Buffer 5X Taq Mn Buffer (100 mM Tris-Cl pH 7.5, 75 mM sodium isocitrate, 10 mM $MnCl_2$, 250 mM sodium chloride) was used, and the Dye-Terminator Mix consisted of 3.6 uM ddG-5R110, 2.7 uM ddA-5R6G, 43.2 uM ddT-6TMR, and 28.8 uM ddC-6ROX. Over 450 bases of the M13 plasmid were correctly identified by the base calling routine of the Model 370A automated sequencer.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A method of distinguishing polynucleotides having different 3'-terminal dideoxynucleotides in the chain termination method of DNA sequencing, the method comprising the steps of:

forming a mixture of a first, a second, a third, and a fourth class of polynucleotides, each polynucleotide in the first class having a 3'-terminal dideoxyadenosine and being labeled with a first dye selected from the going consisting of tetramethylrhodamine, rhodamine X, rhodamine 6G, and rhodamine 110; each polynucleotide in the second class having a 3'-terminal dideoxycytidine and being labeled with a second dye selected from the group consisting of tetramethylrhodamine, rhodamine X, rhodamine 6G, and rhodamine 110; each polynucleotide in the third class having a 3'-terminal dideoxyguanosine and being labeled with a third dye selected from the group consisting of tetramethylrhodamine, rhodamine X, rhodamine 6G, and rhodamine 110; and each polynucleotide in the fourth class having a 3'-terminal dideoxythymidine and being labeled with a fourth dye selected from the group consisting of tetramethylrhodamine, rhodamine X, rhodamine 6G, and rhodamine 110; wherein each class of polynucleotide in the mixture is labeled with a different dye;

electrophoretically separating on a gel the polynucleotides in the mixture so that bands of similarly sized polynucleotides are formed;

illuminating with an illumination beam the bands on the gel, the illumination beam being capable of causing the dyes to fluoresce; and identifying the classes of the polynucleotides in the bands by the fluorescence or absorption spectrum of the dyes.

2. The method of claim 1 wherein said 3'-terminal dideoxyadenosine is 2',3'-dideoxy-7-deazaadenosine and said first dye is attached by way of a linking group to a 7 carbon atom thereof; said 3'-terminal dideoxycytidine is 2',3'-dideoxycytidine and said second dye is attached by way of a linking group to a 5 carbon atom thereof; said 3'-terminal dideoxyguanosine is selected from the group consisting of 2',3'-dideoxy-7-deazaguanosine and 2',3'-dideoxy-7-deazainosine and said third dye is attached by way of a linking group to a 7 carbon atom thereof; and said 3'-terminal dideoxythymidine is 2',3'-dideoxyuridine and said fourth dye is attached by way of a linking group to a 5 carbon atom thereof.

3. The method of claim 2 wherein said linking group is 3-carboxyamino-1-propynyl and links said 7 carbon atoms of said 2',3'-dideoxy-7-deazaadenosine and said dideoxyguanosine selected from the group consisting of 2',3'-dideoxy-7-deazaguanosine and 2',3'-dideoxy-7-deazainosine to a 5 or 6 carbon atom of said first and third dyes, respectively, and links said 5 carbon atoms of said dideoxycytidine and said dideoxyuridine to a 5 or 6 carbon atom of said second and fourth dyes, respectively.

4. The method of claim 3 further including the step of extending from a primer a plurality of polynucleotides by means of a DNA polymerase in the presence of dideoxyadenosine triphosphate, dideoxycytidine triphosphate, a dideoxyguanosine triphosphate, and a dideoxythymidine triphosphate to form said first, second, third, and fourth classes of polynucleotides.

5. The method of claim 4 wherein said DNA polymerase is selected from the group consisting of Taq DNA polymerase and T7 DNA polymerase.

6. The method of claim 5 wherein said 2',3'-dideoxy-7-deazaadenosine is attached to said 5 carbon atom of rhodamine 6G, said 2',3'-dideoxycytidine is attached to said 6 carbon atom of rhodamine X, said dideoxyguanosine selected from the group consisting of 2',3'-dideoxy-7-deazaguanosine and 2',3'-dideoxy-7-deazainosine is attached to said 5 carbon atom of rhodamine 110, and said 2',3'-dideoxyuridine is attached to said 6 carbon atom of tetramethylrhodamine.

7. The method of claim 5 wherein said 2',3'-dideoxy-7-deazaadenosine is attached to said 6 carbon atom of rhodamine X, said 2',3'-dideoxycytidine is attached to said 5 carbon atom of rhodamine 6G, said dideoxyguanosine selected from the group consisting of 2',3'-dideoxy-7-deazaguanosine and 2',3'-dideoxy-7-deazainosine is attached to said 5 carbon atom of rhodamine 110, and said 2',3'-dideoxyuridine is attached to said 6 carbon atom of tetramethylrhodamine.

8. The method of claim 5 wherein said 2',3'-dideoxy-7-deazaadenosine is attached to said 6 carbon atom of rhodamine X, said 2',3'-dideoxycytidine is attached to said 5 carbon atom of rhodamine 110, said dideoxyguanosine selected from the group consisting of 2',3'-dideoxy-7-deazaguanosine and 2',3'-dideoxy-7-deazainosine is attached to said 6 carbon atom of tetramethylrhodamine, and said 2',3'-dideoxyuridine is attached to said 5 carbon atom of rhodamine 6G.

9. The method of claim 5 wherein said 2',3'-dideoxy-7-deazaadenosine is attached to said 5 carbon atom of rhodamine 6G, said 2',3'-dideoxycytidine is attached to said 5 carbon atom of rhodamine 110, said dideoxyguanosine selected from the group consisting of 2',3'-dideoxy-7-deazaguanosine and 2',3'-dideoxy-7-deazainosine is attached to said 6 carbon atom of rhodamine X, and said 2',3'-dideoxyuridine is attached to said 6 carbon atom of tetramethylrhodamine.

10. The method of claim 5 wherein said 2',3'-dideoxy-7-deazaadenosine is attached to said 6 carbon atom of rhodamine X, said 2',3'-dideoxycytidine is attached to said 6 carbon atom of tetramethylrhodamine, said dideoxyguanosine selected from the group consisting of 2',3'-dideoxy-7-deazaguanosine and 2',3'-dideoxy-7-deazainosine is attached to said 5 carbon atom of rhodamine 6G, and said 2',3'-dideoxyuridine is attached to said 5 carbon atom of rhodamine 110.

* * * * *